United States Patent [19]

Holmgren et al.

[11] Patent Number: 5,254,743

[45] Date of Patent: Oct. 19, 1993

[54] SOLID BASES AS CATALYSTS IN ALDOL CONDENSATIONS

[75] Inventors: Jennifer S. Holmgren, Bloomingdale; Blaise J. Arena, Chicago, both of Ill.

[73] Assignee: UOP, Des Plaines, Ill.

[21] Appl. No.: 987,838

[22] Filed: Dec. 9, 1992

[51] Int. Cl.$^5$ .................. C07C 45/73; C07C 45/72
[52] U.S. Cl. ................... 568/463; 568/461; 568/459; 568/462; 568/464; 568/884
[58] Field of Search ............... 568/461, 463, 464, 876, 568/878, 880, 459

[56] References Cited

U.S. PATENT DOCUMENTS

| | | | |
|---|---|---|---|
| 3,248,428 | 4/1966 | Porter, Jr. et al. | 568/463 |
| 4,617,419 | 10/1986 | Wiener et al. | 568/463 |
| 4,943,663 | 7/1990 | Diekhaus et al. | 568/463 |
| 5,144,089 | 9/1992 | Arena et al. | 568/463 |

OTHER PUBLICATIONS

Nakatsuka et al., *Bull. Chem. Soc. Japan*, 52, 2449 (1979).
W. T. Reichle, *J. of Catalysis*, 94, 547 (1985).
E. Suzuki & Y. Ono, *Bull. Chem. Soc. Japan*, 61, 1008 (1988).
Nunan et al., *J. of Catalysis*, 116, 222 (1989).
A. Corma & coworkers, *Applied Catalysis*, 59, 237 (1990).
A. Corma & R. N. Martin-Aranda, *J. Catalysis*, 130, 130 (1991).

*Primary Examiner*—Werren B. Lone
*Attorney, Agent, or Firm*—Thomas K. McBride; Eugene I. Snyder

[57] ABSTRACT

Solid solutions of a class of divalent metal oxides and a class of trivalent metal oxides resulting from calcination of layered double hydroxides related to hydrotalcite have been prepared with a surface area in excess of 150 m$^2$/g. Such high surface area materials are found to be quite effective in the aldol condensation of aldehydes and ketones, and in particular in the conversion of n-butyraldehyde to 2-ethyl-2-hexenal in high yield and with good selectivity in a liquid phase reaction at temperatures under about 200° C. Variants can be devised where the aldol condensation product, an α,β-unsaturated aldehyde or ketone, is concurrently reduced to the saturated alcohol under process conditions.

31 Claims, No Drawings

SOLID BASES AS CATALYSTS IN ALDOL CONDENSATIONS

BACKGROUND OF THE INVENTION

The world-wide production of 2-ethylhexanol-1, which is prepared from 2-ethyl-2-hexenal, is greater than all alcohols other than those containing from 1 to 4 carbon atoms, due mainly to the widespread use of its carboxylic acid esters as a plasticizer, especially in polyvinylchloride. Other uses of this 8-carbon alcohol include the production of intermediates for acrylic surface coatings, diesel fuel and lube oil additives, and surfactants. 2-Ethylhexanol-1 is prepared from n-butyraldehyde as the feedstock, where the latter is the highest volume oxide chemical produced, via the aldol condensation of n-butyraldehyde to 2-ethyl-2-hexenal followed by reduction of both the olefin and aldehyde moieties,

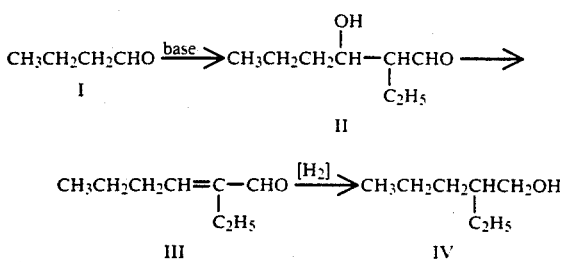

where the actual aldol condensation is represented by the conversion I to II.

The aldol condensation of aldehydes is a well known and time honored reaction employed for many years in the production of several commercially important materials in addition to 2-ethylhexanol-1, for example, the formation of isophorone and mesitylene oxide from acetone. The reaction is not merely base catalyzed, but usually needs a strong base catalyst in order to proceed satisfactorily. Although the aldol product corresponding to II may often be isolated, its dehydration to III is usually facile under the reaction conditions, and accordingly it is most frequently the alpha, beta-unsaturated aldehyde III which is the isolated reaction product.

Often the strong bases used as catalysts in aldol condensation are the alkali metal hydroxides, especially under aqueous or partly aqueous conditions. It should be apparent that the use of alkali metal hydroxides does not lend itself to the adaptation of aldol condensation as a continuous process, in large part because of the hydroxides having unfavorable properties when used as a fixed bed. Yet development of a continuous process for the production of 2-ethyl-2-hexenal and other aldol condensation products is not merely of great interest but rather is of high priority, because of the well-known advantages of fixed bed continuous processes generally and because it would minimize environmental problems associated with the disposal of a strong base as well as minimizing corrosion difficulties caused by a strong aqueous base.

The desirability of a strong base suitable for use as a fixed bed previously has been recognized and has led to the use of such materials, inter alia, as sodium on alumina and potassium on graphite. Because of the severe limitations of such strong bases in a fixed bed, more recent attention has turned to clays and clay-like materials as suitable alternatives.

Hydrotalcite is a clay with the ideal unit cell formula of $Mg_6Al_2(OH)_{16}(CO_3).4H_2O$, and closely related analogs with variable magnesium/aluminum ratios may be readily prepared. Nakatsuka et al., *Bull. Chem. Soc. Japan*, 52, 2449 (1979) has described the catalytic use of "calcined synthetic hydrotalcite" with varying molar ratios of $MgO/Al_2O_3$ in the batch mode polymerization of beta-propylactone. More extensive work was reported later on the use of "synthetic hydrotalcite" in various base-catalyzed reactions by W. T. Reichle, *J. of Catalysis*, 94, 547 (1985), who found that aldol condensations were readily catalyzed by "synthetic hydrotalcite" compositions having Mg/Al ratios from 1.3 to 6.3, although the Mg/Al ratio did not appear to have a significant effect on either its catalytic activity or efficiency. From deuterium exchange studies Reichle also concluded that the $pK_a$ of hydrotalcite was between 35 and 45. E. Suzuki and Y. Ono, *Bull. Chem. Soc, Japan*, 61, 1008 (1988), reported on the aldol condensation between formaldehyde and acetone using as catalysts two quite different types of hydrotalcite-like materials, both being derived from hydrotalcite itself. In one series of catalysts the carbonate moiety of hydrotalcite was exchanged by $NO_3^-$, $SO_4^{2-}$, or $CrO_4^{2-}$, and in the other series there was isomorphous substitution of $Mg^{2+}$—$Al^{3+}$ by $Li^+$—$Al^{3+}$, $Co^{2+}$—$Al^{3+}$, $Ni^{2+}$—$Al^{3+}$, or $Zn^{2+}$—$Cr^{3+}$. At 500° C. reaction temperature none of the foregoing appeared to lead to increased acetone conversion although some slight increase in selectivity (especially at lower conversion) was observed. Nunan et al., *J. of Catalysis*, 116, 222 (1989), has prepared related materials by isomorphous substitution of Mg by Cu and Zn, and of Al by Cr or Ga.

Before proceeding it appears advisable to prevent semantic obfuscation by defining several terms, using first a specific example and then generalizing by analogy. Although "hydrotalcite" is most properly applied to a clay of composition $Mg_6Al_2(OH)_{16}(CO_3).4H_2O$ often it has been used to describe related layered double hydroxides with varying Mg/Al ratios. However, after calcination of the layered double hydroxides the resulting materials are better described as solid solutions of magnesium oxide and aluminum oxide. That is, calcination destroys the layered structure characteristic of hydrotalcite and affords a solid solution. But the terminology as applied to such solid solutions often retains the "hydrotalcite" name, as in, for example, "synthetic hydrotalcites". In this application henceforth we shall try to be consistent in using the term "solid solution" of, e.g., magnesium oxide and aluminum oxide, to describe such calcined synthetic materials. The second point involves the use of the term "Mg/Al". In this application Mg/Al shall be the number ratio of magnesium to aluminum atoms in a solid solution of magnesium oxide and aluminum oxide. While this definition has been previously employed by, for example, Reichle, others have used a different definition for the Mg/Al ratio.

We can generalize the foregoing characterization to the family of materials, described more fully within, having the general formula $(M^a)_x(M^b)_y(OH)_zA_q.rH_2O$, where $M^a$ is a divalent metal or combination of divalent metals, $M^b$ is a trivalent metal or a combination of trivalent metals, and A is an anion, often carbonate. Such materials are layered double hydroxides. However, after calcination of the layered double hydroxide the resulting product is a solid solution of the two oxides, $M^aO$ and $M^b_2O_3$. We shall retain this distinction between layered double hydroxides and solid solutions throughout this application.

Shortly after Reichle's work, Corma and coworkers described their investigations into the use of certain zeolites as base catalysts; A. Corma and coworkers, *Applied Catalysis*, 59, 237 (1990). The effect of a series of alkali metal exchanged X and Y zeolites was investigated in batch reactions in catalyzing the condensation of benzaldehyde with ethylcyanoacetate and diethyl malonate, where it was determined that the reactivity of the metal-exchanged zeolites was in the order cesium > potassium > sodium > lithium, and X > Y. The $pK_b$'s of these materials were said to be between about 10.3 and 13, which is far less than that given by Reichle for his "synthetic hydrotalcites". In related work [A. Corma and R. N. Martin-Aranda, *J. Catalysis*, 130, 130 (1991)], Corma exchanged the magnesium ions on the edges of the octahedral sheet in sepiolite with alkali metal ions to afford materials also effective as base catalysts in the foregoing condensation, but noted that the basicity of the resulting materials also was far less than that of hydrotalcite.

Our objective was the development of a continuous process for the aldol condensation of suitable carbonyl compounds, especially in the liquid phase. It was important that the process be continuous and employ a fixed bed of catalyst. Therefore the catalyst had to possess suitable flow properties, compressibility, and so forth, consistent with a liquid flow. It is important to note that whereas some aldol condensations, such as the condensation of n-butyraldehyde, are performed in the vapor phase, it was quite desirable that the new process also be applicable to liquid phase aldol condensation. It also is important that the aldol condensation proceed in relatively high yield, with good selectivity, and at modest temperatures, say less than 200° C. Since water is a reaction product, it is important that the catalysts exhibit hydrothermal stability. We have found that solid solutions of a divalent metal oxide and a trivalent metal oxide with high surface area appear to satisfy the foregoing criteria in all respects.

SUMMARY OF THE INVENTION

The purpose of this invention is to develop a continuous process for the aldol condensation of suitable carbonyl compounds using as a solid bed a basic catalyst which is a high surface area solid solution of certain divalent metal oxides and trivalent metal oxides, especially where the process is applicable also to a liquid phase condensation. In one embodiment the base catalyst has the formula $(M^aO)_x(M^b_2O_3)_y$ and is a solid solution of the oxides of the divalent metal $M^a$ and trivalent metal $M^b$, having a surface area greater than 150 m²/g. In a more specific embodiment the solid base catalyst has a surface area between 150 and 350 m²/g. In a still more specific embodiment the trivalent metal is aluminum. In another specific embodiment the reaction temperature is between about 80° and about 200° C. Other variants and embodiments will be apparent from the ensuing description.

DESCRIPTION OF THE INVENTION

Our invention is based on the observation that solid solutions of certain divalent metal oxides and trivalent metal oxides having a surface area over about 150 m²/g are quite effective in promoting the aldol condensation of carbonyl compounds, especially aliphatic aldehydes, and more particularly n-butyraldehyde, with both high conversion and high selectivity at temperatures under 200° C. This observation affords the opportunity to devise a continuous process for the preparation of the aldol condensation products of these carbonyl compounds, and in particular for the preparation of 2-ethyl-2-hexenal, the dehydrated aldol condensation product of n-butyraldehyde, whether the process be a vapor or liquid phase condensation. The basic process can be further modified so as to reduce the aldol condensation product to the saturated alcohol.

The carbonyl compounds used as feedstocks in the practice of this invention have the formula $R_mCH_2CR_nO$. By far the most common group of such carbonyl compounds undergoing the aldol condensation reaction is that of the aldehydes, i.e. those compounds where $R_n = H$. In one variant for the class of aldehydes $R_m$ is an alkyl or alkenyl moiety, either linear or branched, having from 1 to 20 carbon atoms. Variants where $R_m$ has from 1 to 10 carbon atoms are preferred, and those where $R_m$ has between 2 and 4 carbon atoms are even more desirable. Although $R_m$ may be an alkenyl moiety, the variant where $R_m$ is a saturated alkyl moiety is the more usual one, and the most usual case is that where $R_m$ is a linear, saturated alkyl group having between 2 and 4 carbon atoms. The case where $R_m$ is an ethyl group, i.e., the aldehyde is n-butyraldehyde, is especially preferred because of the particular importance of its aldol condensation product.

In another variant $R_m$ is an aralkyl moiety whose alkyl portion is linear with a carbon number from 1 through 20, and especially having from 1 to 10 carbon atoms in the alkyl chain. The aryl group may be anywhere on the alkyl chain; its position is in no way restrictive. That variant where the aryl group is phenyl is the most common one, although substituted phenyl and higher aromatic systems, such as naphthyl, anthryl, phenanthryl, biphenylyl, and so forth, may be used without prejudice. As will be emphasized below the continuous aldol condensation often is most desirably performed in the liquid phase, therefore in this modification whatever aldehyde is used flows through a fixed catalyst bed in the liquid phase.

Although aldehydes form the most common class of aldol reactants, ketones having the given formula also may be used in the practice of this invention. In this case $R_n$ is generally selected from the group defined by $R_m$, although $R_n$ and $R_m$ need not be the same. The case where $R_n$ is an alkyl moiety, especially a saturated alkyl moiety having from 1 to 20 carbon atoms, is a favored variant, and that variant where the saturated alkyl moiety contains from 1 to 10 carbons, particularly 1 to 4 carbons, is especially favored. For ketones another desirable variant is that where $R_n$ is an aromatic moiety such as phenyl, substituted phenyl, and to a lesser degree higher aromatic systems such as naphthyl, anthryl, phenanthryl, biphenylyl, and so forth.

The novel base catalysts employed in our invention are solid solutions of a divalent metal oxide and a trivalent metal oxide having the general formula $(M^aO)_x(M^b_2O_3)_y$, and with a surface area greater than 150 m²/g, usually between 250 and 350 m²/g. The solid solutions result from calcination of synthetic hydrotalcite-like materials whose general formula may be expressed as $(M^a)_x(M^b)_y(OH)_zA_q \cdot rH_2O$. $M^a$ is a divalent metal or combination of divalent metals selected from the group consisting of magnesium, calcium, barium, nickel, cobalt, iron, copper and zinc. $M^b$ is a trivalent metal or combination of trivalent metals selected from the group consisting of aluminum, gallium, chromium, iron, and lanthanum. $A_q$ is an anion, most usually carbonate although other anions may be employed equivalently, especially anions such as nitrate, sulfate, chloride, bromide, hydroxide, and chromate. The case where $M^a$ is magnesium, $M^b$ is aluminum, and A is carbonate corresponds to the hydrotalcite series.

It is preferable that the $M^aO/M^b{}_2O_3$ solid solution has a surface area at least about 150 m$^2$/g, more preferably at least 200 m$^2$/g and it is even more preferable that it be in the range from 300 to 350 m$^2$/g. Although the unusually high surface area of the solid solutions of our invention appears to be an important property related to the unique functional characteristics of the catalysts of our invention, the ratio of the divalent and trivalent metals also is important, although it does not appear to be determinative of operability. Thus, the ratio x/y can vary between about 2 and about 10, with the interval of 3 to about 6 being preferred. We have found that such catalysts afford excellent conversion of the aldehyde or ketone to its aldol condensation product with good selectivity throughout a wide range of conversion at quite reasonable liquid hourly space velocities, or productivity.

We wish to emphasize that in the catalysts of our invention both $M^a$ and $M^b$ may be mixtures of metals belonging to the class defined by $M^a$ and $M^b$, respectively. So, for example, $M^a$ may be pure nickel or may be both nickel and magnesium, or even nickel-magnesium-cobalt. Similarly, $M^b$ may be solely aluminum or a mixture of aluminum and chromium, or even a mixture of three trivalent metals such as aluminum, chromium, and gallium. In such cases the solid solutions still can be represented as $(M^aO)_x(M^b{}_2O_3)_y$, where x refers to the relative mole proportion of all of the divalent metal oxides and y refers to the relative mole proportion of all of the trivalent metal oxides. For convenience, and without loss of generality, y may be assigned the value of 1 and the solid solutions of this invention may then be represented as $(M^aO)_x(M^b{}_2O_3)$, where x varies between about 2 and about 10.

The solid basic catalysts of our invention with their unique properties result from an atypical preparation of these materials, especially as to their layered double hydroxide, hydrotalcite-like precursors. In particular, as described in more detail within, the precursor gel is prepared at a temperature not exceeding about 10° C., and preferably is prepared in the temperature interval between about 0° and 5° C. In addition, the crystallization time is kept short, on the order of an hour or two at 65° C., to afford layered double hydroxides whose calcination leads to materials of unusual hydrothermal stability, as discussed below. Calcination of the layered double hydroxide is effected at temperatures between about 400° and about 750° C. to afford the solid solutions effective as aldol condensation catalysts in the practice of this invention.

The unusual stability of the solid solutions of a divalent metal oxide and a trivalent metal oxide prepared according to the foregoing procedure is evidenced by the fact that spinel formation is not seen until calcination temperatures of about 800° C., whereas in the prior art hydrotalcite-type layered double hydroxides the spinel phase begins to appear at a calcination temperature of about 600° C. In addition, the solid basic catalysts of our invention show greater product homogeneity as evidenced by their resistance to spinel formation. The increased hydrothermal stability of our solid basic catalysts is important since water is generally one of the reaction products accompanying aldol condensation, and although the reaction does not proceed in an aqueous solution, where hydrothermal stability is most important, the catalyst is continually exposed to significant concentrations of water.

The aldol condensation of the aldehydes and ketones of this invention is performed at a temperature as low as about 50° C. up to as high as about 300° C., usually between about 80° and about 200° C., and most commonly between about 100° and 190° C. Where a liquid phase reaction is desired, the reaction pressure is important only insofar as ensuring that the reaction occur in the liquid phase. So, for example, to ensure a liquid phase reaction for the lower aldehydes and ketones pressures up to a few thousand psig may be employed, especially at higher reaction temperatures, but as the molecular weight of the aldehyde increases lower pressures are needed to ensure complete liquid phase reaction. It will be readily appreciated that the appropriate pressure necessary to maintain a liquid phase throughout the reactor can be readily determined by one skilled in the art and will depend on the feedstock molecular weight and reaction temperature, as stated above. The liquid hourly space velocity, or the feed rate of reactant, is not critical to the success of this invention but is rather a variable which is optimized with respect to productivity. For example, it has been found that liquid hourly space velocities on the order of 2–10 form a convenient range within which to work. But it is to be emphasized that these are not limiting figures but are rather only illustrative of the characteristics of the process carried out according to our invention.

The aldol condensation product is a beta-hydroxy carbonyl compound, i.e., a beta-hydroxy ketone or beta-hydroxy aldehyde. It is well known that this structural unit readily undergoes dehydration where possible to the corresponding alpha, beta-unsaturated carbonyl compound, (an $\alpha$, $\beta$-unsaturated aldehyde or ketone), i.e., a compound having the structural unit C=C—C=O; see, e.g., structure III supra. Consequently it is quite common that the major product observed in an aldol condensation is the corresponding $\alpha$, $\beta$-unsaturated aldehyde or ketone rather than the $\beta$-hydroxy aldehyde or ketone.

As previously noted, 2-ethyl-2-hexenal is particularly important in the preparation of 2-ethylhexanol-1 by hydrogenation of the olefinic and aldehydic moieties of the unsaturated aldehyde, and it is possible to devise a process where aldol condensation, dehydration of the aldol product, and hydrogenation occur concurrently in the same catalyst bed. For example, metals having hydrogenation activity can be deposited largely in the interior of catalyst particles previously described to afford a metal-modified catalyst. Feedstock subsequently can be contacted with the metal-modified catalyst in the presence of hydrogen at pressures of 50 up to 1000 psig, and at temperatures between about 80° C. and about 200° C., conditions which effect consecutively aldol condensation, dehydration of the aldol product, and hydrogenation.

Another kind of dual function catalyst results from a solid solution where some of the divalent metal $M^a$ is replaced by a divalent metal cation M'(II) which, under its conditions of use, is partially reduced to the zerovalent metal, M'(O), having hydrogenation activity and which behaves under reaction conditions to catalyze reduction of the unsaturated centers. Upon reduction of M'(II) the zerovalent metal formed is no longer in the framework, but it remains active as a hydrogenation catalyst. Examples of metals M' which may be used include platinum, iridium, osmium, palladium, rhenium, ruthenium, rhodium, and nickel, where palladium and nickel are especially preferred metals in this variant of our invention. In both the case described here as well as that in the prior paragraph the resulting process is one where, for example, an aldehyde of this invention, such as butyraldehyde, is the feedstock along with hydrogen and a saturated alcohol with twice as many carbons as the aldehyde is the product, as exemplified by 2-ethylhexanol-1.

The preparation of extrudates having a skewed metal distribution is known to a person of ordinary skill to result either in a product having the metal concentrated in a core at the center of the extrudate, or alternatively in a circular "shell" around a core of the support in which the metal is impregnated. M. Komiyama, *Catalysis Reviews, Science and Engineering*, V. 27, 341 (1985). One could prepare as a suitable catalyst a metal-impregnated support as an extrudate where the support is a solid solution of this invention having a skewed metal distribution resulting from either of the foregoing methods, where the metal impregnating the support has hydrogenation activity. Prime examples of metals, particularly in the zerovalent state, commonly used to catalyze hydrogenation include the Group VIII metals of platinum, palladium, nickel, rhodium, rhenium, iridium, and osmium. In many cases a combination of metals is used, both combinations of Group VIII metals alone as well as one or more Group VIII metals combinations of Group VIII metals alone as well as one or more Group VIII metals with metals such as cobalt, iron, copper, and so on. Concentrations of the metal with hydrogenation function may be as low as about 0.01 weight percent based on finished catalyst to as a high as about 10 weight percent, depending upon the hydrogenation activity of the metal and conditions contemplated for its use. Most commonly the catalyst will contain from about 0.1 up to as high as 5 weight percent hydrogenation metal. Whatever the method of preparing an extrudate with a skewed metal distribution, the initial aldol condensation and aldol product dehydration would occur largely in the metal-free portion of the catalyst, and subsequent diffusion of the latter product, as e.g. 2-ethyl-2-hexenal, into the portion bearing the metal having hydrogenation activity would result in subsequent reduction of the unsaturated olefinic and aldehydic linkages under the reaction conditions.

One can formulate different rationales for the two extreme types of skewed metal distribution in metal-impregnated solid solutions of the type described above. In the case where the metal is concentrated in a core at the center of the catalyst, one can envision the aldehyde undergoing aldol condensation-dehydration in the catalyst pores with the olefinic product subsequently diffusing further into the catalyst interior such that only, or virtually only, the dehydrated aldol product comes into contact with the metal effecting hydrogenation. A potential difficulty with that scenario is the requirement that the aldol product, once formed, does not diffuse out of the catalyst particle, for once it diffuses out of the catalyst particle the dehydrated aldol product will have to pass through a very basic medium in subsequently diffusing into the catalyst particle prior to encountering the hydrogenation metal, possible leading to undesirable side reactions.

In an eggshell metal distribution reactants would first encounter the hydrogenation-active metal prior to diffusing into the exclusively basic environment of the catalyst. Where the metal has high selectivity for olefinic hydrogenation vis-a-vis carbonyl (aldehydic or ketonic) hydrogenation this arrangement could be quite salutary, so long as the saturated aldehyde or ketone is desired as the final product. It should be clear that a high selectivity is necessary for effective operation, since any reactant would likely repeatedly pass through, or come into contact with, the hydrogenation metal in a continuous process.

A combination of the two also might prove beneficial in a well-designed reactor. For example, in that part of the catalyst bed where most of the aldol condensation-dehydration occurs the hydrogenation metal may be deposited in a central core, whereas in that part of the bed where the mixture is largely the dehydrated aldol condensation product the hydrogenation metal may be present in an eggshell distribution at or near the surface. In this way the advantages of each distribution may be maximized while their disadvantages are minimized. We note that in this scenario the metal need not be selective for olefin reduction, and in fact this arrangement may be quite advantageous in forming the saturated alcohol corresponding to IV and its analogs.

Another alternative is to prepare two different kinds of solid solutions, where one $(M^aO)_x(M^b_2O_3)_{y/2}$ contains as $M^a$ only metals without hydrogenation activity, and where the other solid solution of similar formula contains a metal, $M^{a'}$, effective to catalyze reduction, as for example nickel, palladium, platinum, rhodium, rhenium, ruthenium, indium, and osmium, particularly nickel and palladium. The separate materials could be coextruded using a double dye, the finished dough dried and calcined as previously described, to afford the final catalyst.

The following examples are only illustrative of our invention and do not limit it in any way. Other embodiments and variants will be apparent to one of ordinary skill in the art.

EXAMPLE 1

Preparation of Magnesium Oxide-Aluminum Oxide Solid Solution

A 2L, 3-necked round bottomed flask was equipped with an addition funnel, a thermometer, a mechanical stirrer, and a heating mantle. To this flask was added a solution containing 610 g of water, 60 g of $Na_2CO_3.H_2O$ and 71 g of NaOH and the contents were cooled to <5° C. The addition funnel was charged with a solution of 345 g water, 77 g $Mg(NO_3)_2.6H_2O$ and 75 g $Al(NO_3)_3.9H_2O$ and this solution was added over a period of 4 hours. The solution temperature was maintained at <5° C. throughout the addition and the resulting slurry was stirred for 1 hour at <5° C. The addition funnel was replaced by a reflux condenser and the slurry was heated to 60°±5° C. for 1 hour. The slurry was then cooled to room temperature and the solids recovered by filtration. The solids were washed with 10L of hot deionized water. The solids were then dried at 100° C. for 16 hours and this product was characterized as hydrotalcite by its x-ray diffraction (XRD) pattern. After crushing, the solid was calcined at 450° C. for 12 hours in a muffle furnace with an air flow. This product was characterized as a MgO—Al$_2$O$_3$ solid solution (Mg/Al=1.5) by XRD. The BET surface area for this material was 285 m$^2$/g. Materials with a different Mg/Al ratio may be prepared by similar means, changing only the relative molar ratio of Mg(NO$_3$)$_2$.6H$_2$O and Al(NO$_3$)$_3$.H$_2$O.

EXAMPLE 2

Preparation of Mg/Ni/Al Layered Double Hydroxide 1. 5% Mg. A 2 L, 3-necked round bottomed flask was equipped with a reflux condenser, a thermometer, a mechanical stirrer, and a Glass Col heating mantle. To this 3-neck flask was added a solution containing 585 g of water, 60 g of Na$_2$CO$_3$.H$_2$O and 71 g of NaOH. This flask was cooled to <5° C. An addition funnel was charged with a solution of 375 g water, 6.5 g Mg(NO$_3$)$_2$.H$_2$O, 139 g Ni(NO$_3$)$_2$.6H$_2$O and 93 g Al(NO$_3$)$_3$.9H$_2$O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60° C.±5° C. for 1 hour. The slurry was then cooled to room temperature and the solids recovered by filtration. The solids were washed with 10 L of hot DI water. The solids were then dried at 100° C. for 16 hours. This product was characterized as hydrotalcite by its XRD pattern. After crushing, the solid was calcined at 450° C. for 12 hours in a muffle furnace with an air flow. This product was characterized as a MgO—NiO—Al$_2$O$_3$ solid solution by XRD. The BET surface area for this material was 205 m$^2$/g. Alternatively, the hydrotalcite slurry/paste can be extruded prior to drying and calcining.

2. 25% Mg. A 2 L, 3-necked round bottomed flask was equipped with a reflux condenser, a thermometer, a mechanical stirrer, and a Glass Col heating mantle. To this 3-neck flask was added a solution containing 585 g of water, 60 g of Na$_2$CO$_3$.H$_2$O and 71 g of NaOH. This flask was cooled to <5° C. An addition funnel was charged with a solution of 378 g water, 32.5 g Mg(NO$_3$)$_2$.6H$_2$O, 110 g Ni(NO$_3$)$_2$.6H$_2$O and 93 g Al(NO$_3$)$_3$9H$_2$O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60° C.±5° C. for 1 hour. The slurry was then cooled to room temperature and the solids recovered by filtration. The solids were washed with 10 L of hot DI water. The solids were then dried at 100° C. for 16 hours. This product was characterized as hydrotalcite by its XRD pattern. After crushing, the solid was calcined at 450° C. for 12 hours in a muffle furnace with an air flow. This product was characterized as a MgO—NiO—Al$_2$O$_3$ solid solution by XRD. The BET surface area for this material was 199 m$^2$/g. Alternatively, the hydrotalcite slurry/paste can be extruded prior to drying and calcining.

3. 75% Mg. A 2 L, 3-necked round bottomed flask was equipped with a reflux condenser, a thermometer, a mechanical stirrer, and a Glass Col heating mantle. To this 3-neck flask was added a solution containing 592 g of water, 60 g of Na$_2$CO$_3$.H$_2$O and 71 g of NaOH. This flask was cooled to <5° C. An addition funnel was charged with a solution of 375 g water, 65 g Mg(NO$_3$)$_2$.6H$_2$O, 73.5 g Ni(NO$_3$)$_2$.6H$_2$O and 93 g (Al(NO$_3$)$_3$.9H$_2$O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60° C.±5° C. for 1 hour. The slurry was then cooled to room temperature and the solids recovered by filtration. The solids were washed with 10 L of hot DI water. The solids were then dried at 100° C. for 16 hours. This product was characterized as hydrotalcite by its XRD pattern. After crushing, the solid was calcined at 450° C. for 12 hours in a muffle furnace with an air flow. This product was characterized as a MgO—NiO—Al$_2$O$_3$ solid solution by XRD. The BET surface area for this material was 212 m$^2$/g. Alternatively, the hydrotalcite slurry/paste can be extruded prior to drying and calcining.

EXAMPLE 3

Preparation of Co/Ni/Al Layered Double Hydroxide (20% Co)

A 2 L, 3-necked round bottomed flask was equiped with a reflux condenser, a thermometer, a mechanical stirrer, and a Glass Col heating mantle. To this 3-neck flask was added a solution containing 618 g of water, 58 g of Na$_2$CO$_3$.H$_2$O and 72 g of NaOH. This flask was cooled to <5° C. An addition funnel was charged with a solution of 342 g water, 35 g Co(NO$_3$)$_2$.6H$_2$O, 139 g Ni(NO$_3$)$_2$.6H$_2$O and 75 g Al(NO$_3$)$_3$.9H$_2$O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60°±5° C. for 1 hour. The slurry was then cooled to room temperature and the solids recovered by filtration. The solids were washed with 10 L of hot DI water. The solids were then dried at 100° C. for 16 hours. This product was characterized as hydrotalcite by its XRD pattern. After crushing, the solid was calcined at 450° C. for 12 hours in a muffle furnace with an air flow. This product was characterized as a CoO—NiO—Al$_2$O$_3$ solid solution by XRD. The BET surface area for this material was 209 m$^2$/g. Alternatively, the hydrotalcite slurry/paste can be extruded prior to drying and calcining.

EXAMPLE 4

Preparation of Co/Mg/Al Layered Double Hydroxide 1. 5% Co. A 2 L, 3-necked round bottomed flask was equipped with a reflux condenser, a thermometer, a mechanical stirrer, and a Glass Col heating mantle. To this 3-neck flask was added a solution containing 610 g of water, 60 g of Na$_2$Co$_3$.H$_2$O and 102 g of NaOH. This flask was cooled to <5° C. An addition funnel was charged with a solution of 436 g water, 9 g Co(NO$_3$)$_2$.6H$_2$O, 156 g Mg(NO$_3$)$_2$.6H$_2$O and 81 g Al(NO$_3$)$_3$.9H$_2$O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60° C.±5° C. for 1 hour. The slurry was then cooled to room temperature and the solids recovered by filtration. The solids were washed with 10 L of hot DI water. The solids were then dried at 100° C. for 16 hours. This product was characterized as hydrotalcite by its XRD pattern. After crushing, the solid was calcined at 450° C. for 12 hours in a muffle furnace with an air flow. This product was characterized as a MgO—CoO—Al$_2$O$_3$ solid solution by XRD. The BET surface area for this material was 175 m$^2$/g. Alternatively, the hydrotalcite slurry/paste can be extruded prior to drying and calcining.

2. 20% Co. A 2 L, 3-necked round bottomed flask was equipped with a reflux condenser, a thermometer, a mechanical stirrer, and a Glass Col heating mantle. To this 3-neck flask was added a solution containing 610 g of water, 60 g of Na$_2$Co$_3$H$_2$O and 102 g of NaOH. This flask was cooled to <5° C. An addition funnel was charged with a solution of 435 g water, 44 g Co(NO$_3$)$_2$6H$_2$O, 154 g Mg(NO$_3$)$_2$6H$_2$O and 94 g Al(NO$_3$)$_3$9H$_2$O. The addition funnel was put in place of the reflux condenser. This solution was added over a period of 4 hours. The solution temperature was maintained at <5° C. throughout the addition. This slurry was stirred for 1 hour at <5° C. The addition funnel was removed and the reflux condenser replaced. This solution was heated to 60° C.±5° C. for 1 hour. The slurry was then cooled to room temperature and the solids recovered by filtration. The solids were washed with 10 L of hot DI water. The solids were then dried at 100°0 C. for 16 hours. This product was characterized as hydrotalcite by its XRD pattern. After crushing, the solid was calcined at 450° C. for 12 hours in a muffle furnace with an air flow. This product was characterized as a MgO-CoOAl$_2$O$_3$ solid solution by XRD. The BET surface area for this material was 189 m$^2$/g. Alternatively, the hydrotalcite slurry/paste can be extruded prior to drying and calcining.

EXAMPLE 5

General Method of Continuous Aldol Condensation

The reactor consisted of a feed vessel containing, for example, butyraldehyde as the feedstock, a feed pump for charging the feedstock to the reactor, and the reactor section which was a vertical 7/8 inch ID stainless steel approximately 3 feet in length fitted with a spiral preheater in the lower section of the pipe. The reactor was housed inside a tube furnace and a thermocouple probe extended into the center of the reactor to afford a direct measurement of reaction temperature in the catalyst zone. Five grams of the solid solution of magnesium oxide-aluminum oxide to be tested was mixed with an equal volume of sand and loaded into the reactor above the preheater, with the sand provided to afford improved liquid flow characteristics through the catalyst bed to reduce the likelihood of channeling. The catalyst bed depth was approximately 6 inches. Effluent was collected and analyzed by gas chromatography using a 50 m×0.2 mm ID×0.5 micron methylsilicone film. The instrument was temperature programmed from 50 to 240° C. at 8° C. per minute and held at 240° C. for 10 minutes.

Test runs were initiated using the following procedure. The catalyst bed was treated in the reactor at 500° C. under flowing nitrogen for 2 hours and then cooled to room temperature. With butyraldehyde as the reactant, the feedstock was pumped upflow at 150 grams per hour through the bottom of the reactor with the reactor pressure maintained at 1500 psig. The reactor was then heated to reaction temperature, and when the reactor was liquid full the feed rate was decreased to 50 grams per hour and maintained at that rate.

Typical results for butyraldehyde as the feedstock are presented in Table 1 which show the extent of reaction (conversion) and selectivity of 2-hexenal formation as a function of temperature using as a catalyst material with Mg/Al=1.5 as prepared according to Example 1. Table 2 presents a summary of these results, giving average values of conversion and selectivity at various temperatures.

EXAMPLE 6

Continuous Aldol Condensation, Dehydration, and Hydrogenation

The following may be conducted in a continuous fixed bed system consisting of a liquid feed charger and pump, a hydrogen feed system, a 1" ID vertical tube reactor with furnace, and a gas-liquid separator. The catalyst may be, for example, 1% Pd supported on a solid solution of Al$_2$O$_3$—MgO in such a manner that the Pd resides only in the interior of each catalyst particle. Ten grams of this catalyst may be placed into the reactor below a spiral preheater and fixed in place so that it maintains its position during flow operation. A neat butyraldehyde feed may be charged upflow continuously to the reactor at 30 g/hr. Hydrogen flow may be started upflow to the reactor at a 4:1 mole ratio of H$_2$ to butyraldehyde at 200 psig reactor pressure and the reactor temperature may be brought to 150° C. Within the reactor, aldol condensation of butyraldehyde to 2-ethyl-2-hexenal and hydrogenation to 2-ethylhexanol occur consecutively over the same catalyst bed. Butyraldehyde conversion of 90% with 75% selectivity to 2-ethylhexanol-1 may be achieved.

What is claimed is:

1. A process for conducting the aldol condensation of a carbonyl compound of formula R$_m$CH$_2$CR$_n$O, where R$_m$ is selected from the group consisting of alkyl or alkenyl moieties having from 1 to 20 carbon atoms, or an arylalkyl moiety where the aryl group is a phenyl, substituted phenyl, naphthyl, phenanthryl, or biphenylyl moiety and the alkyl group contains from 1 to 20 carbon atoms, and where R$_n$ is selected from the group consisting of hydrogen, alkyl or alkenyl moieties having from 1 to 20 carbon atoms, or an arylalkyl moiety where the aryl group is a phenyl, substituted phenyl, naphthyl, phenanthryl, or biphenylyl moiety and the alkyl group contains from 1 to 20 carbon atoms, comprising flowing at a temperature between about 50° and about 300° C. a mass of said carbonyl compound through a fixed mass of a solid basic catalyst comprising a solid solution of a divalent first metal oxide and a trivalent second metal oxide having a surface area of at least 150 m$^2$ per gram, said first metal selected from the group consisting of magnesium, calcium, barium, nickel, cobalt, iron, copper, zinc, and any combination thereof, and said second metal selected from the group consisting of aluminum, gallium, chromium, cobalt, iron, lanthanum, and any combination thereof, where said first metal is not exclusively magnesium when said second metal is exclusively aluminum, and recovering from the effluent the aldol condensation products.

2. The process of claim 1 where the first metal is nickel, magnesium, zinc, cobalt, or any combination thereof.

3. The process of claim 1 where the second metal is aluminum.

4. The process of claim 1 where the first metal is nickel, magnesium, zinc, cobalt, or any combination thereof and the second metal is aluminum.

5. The process of claim 1 where $R_n$ is hydrogen and $R_m$ is an alkyl moiety having from 1 to 20 carbon atoms.

6. The process of claim 5 where $R_m$ is an alkyl moiety having from 1 to 10 carbon atoms.

7. The process of claim 5 where $R_m$ is an alkyl moiety having from 2 to 4 carbon atoms.

8. The process of claim 1 where $R_m$ is an arylalkyl moiety, where the aryl group is phenyl or substituted phenyl and the alkyl moiety has from 1 to 20 carbon atoms.

9. The process of claim 8 where $R_m$ is an arylalkyl moiety, where the aryl group is phenyl or substituted phenyl and the alkyl moiety has from 1 to 10 carbon atoms.

10. The process of claim 9 where $R_m$ is an arylalkyl moiety, where the aryl group is phenyl or substituted phenyl and the alkyl moiety has from 2 to 4 carbon atoms.

11. A process for the preparation of the hydrogenated aldol condensation product of a carbonyl compound of formula $R_mCH_2CR_nO$, where $R_m$ is selected from the group consisting of alkyl or alkenyl moieties having from 1 to 20 carbon atoms, or an arylalkyl moiety where the aryl group is a phenyl, substituted phenyl, naphthyl, phenanthryl, or biphenylyl moiety and the alkyl group contains from 1 to 20 carbon atoms, and where $R_n$ is selected from the group consisting of hydrogen, alkyl or alkenyl moieties having from 1 to 20 carbon atoms, or an arylalkyl moiety where the aryl group is a phenyl, substituted phenyl, naphthyl, phenanthryl, or biphenylyl moiety and the alkyl group contains from 1 to 20 carbon atoms, comprising flowing at a temperature between about 50 and about 300° C. at a hydrogen partial pressure from about 50 to about 1,000 psig a mass of said carbonyl compound through a fixed mass of a solid basic catalyst comprising a solid solution of a divalent first metal oxide and a trivalent second metal oxide having a surface area of at least 150 m$^2$ per gram, said first metal selected from the group consisting of magnesium, calcium, barium, nickel, cobalt, iron, copper, zinc, and any combination thereof, and said second metal selected from the group consisting of aluminum, gallium, chromium, cobalt, iron, lanthanum, and any combination thereof, where said first metal is not exclusively magnesium when said second metal is exclusively aluminum, said solid solution being impregnated with a metal having hydrogenation activity which hydrogenates the alpha, beta-unsaturated carbonyl compound, formed as the product to the corresponding saturated alcohol, said metal being deposited in an amount effective to catalyze the hydrogenation of said alpha, beta-unsaturated carbonyl compound to the hydrogenated aldol condensation product, and recovering from the effluent the hydrogenated aldol condensation product.

12. The process of claim 11 where the metal having hydrogenation activity is selected from the group consisting of platinum, palladium, nickel, rhodium, rhenium, ruthenium, iridium, and osmium.

13. The process of claim 12 where the metal having hydrogenation activity is nickel or palladium.

14. The process of claim 11 further characterized in that the catalyst has a skewed distribution of the metal with hydrogenation activity, where said metal is concentrated in a central core.

15. The process of claim 11 further characterized in that the catalyst has a skewed distribution of the metal with hydrogenation activity, where said metal is concentrated in a circular shell around a core of the solid solution.

16. The process of claim 11 where the first metal is nickel, magnesium, zinc, cobalt, or any combination thereof.

17. The process of claim 11 where the second metal is aluminum.

18. The process of claim 11 where the first metal is nickel, magnesium, zinc, cobalt, or any combination thereof and the second metal is aluminum.

19. The process of claim 11 where $R_m$ is an alkyl moiety having from 1 to 10 carbon atoms.

20. The process of claim 11 where $R_m$ is an alkyl moiety having from 2 to 4 carbon atoms.

21. The process of claim 11 where $R_m$ is an arylalkyl moiety, where the aryl group is phenyl or substituted phenyl and the alkyl moiety has from 1 to 20 carbon atoms.

22. The process of claim 11 where $R_m$ is an arylalkyl moiety, where the aryl group is phenyl or substituted phenyl and the alkyl moiety has from 1 to 10 carbon atoms.

23. The process of claim 11 where $R_m$ is an arylalkyl moiety, where the aryl group is phenyl or substituted phenyl and the alkyl moiety has from 2 to 4 carbon atoms.

24. A process for the preparation of the hydrogenated aldol condensation product of a carbonyl compound of formula $R_mCH_2CR_nO$, where $R_m$ is selected from the group consisting of alkyl or alkenyl moieties having from 1 to 20 carbon atoms, or an arylalkyl moiety where the aryl group is a phenyl, substituted phenyl, naphthyl, phenanthryl, or biphenylyl moiety and the alkyl group contains from 1 to 20 carbon atoms, and where $R_n$ is selected from the group consisting of hydrogen, alkyl or alkenyl moieties having from 1 to 20 carbon atoms, or an arylalkyl moiety where the aryl group is a phenyl, substituted phenyl, naphthyl, phenanthryl, or biphenylyl moiety and the alkyl group contains from 1 to 20 carbon atoms, comprising flowing at a temperature between about 50 and about 300° C. at a hydrogen partial pressure from about 50 to about 1,000 psig a mass of said carbonyl compound through a fixed mass of a solid basic catalyst comprising a solid solution of a divalent first metal oxide and a trivalent second metal oxide having a surface area of at least 150 m$^2$ per gram, said first metal selected from the group consisting of magnesium, calcium, barium, nickel, cobalt, iron, copper, zinc, and any combination thereof, and said second metal selected from the group consisting of aluminum, gallium, chromium, cobalt, iron, lanthanum, and any combination thereof, where said first metal is not exclusively magnesium when said second metal is exclusively aluminum, said solid solution containing dispersed therein a zerovalent third metal selected from the group consisting of platinum, iridium, osmium, palladium, rhenium, ruthenium, rhodium and nickel, said zerovalent third metal resulting from the reduction of said third metal oxide originally present in the solid solution, and recovering from the effluent the hydrogenated aldol condensation product.

25. The process of claim 24 where the first metal is nickel, magnesium, zinc, cobalt, or any combination thereof.

26. The process of claim 24 where the second metal is aluminum.

27. The process of claim 24 where the first metal is nickel, magnesium, zinc, cobalt, or any combination thereof and the second metal is aluminum.

28. The process of claim 24 where $R_m$ is an alkyl moiety having from 1 to 10 carbon atoms.

29. The process of claim 24 where $R_m$ is an alkyl moiety having from 2 to 4 carbon atoms.

30. The process of claim 24 where $R_m$ is an arylalkyl moiety, where the aryl group is phenyl or substituted phenyl and the alkyl moiety has from 1 to 20 carbon atoms.

31. The process of claim 24 where $R_m$ is an arylalkyl moiety, where the aryl group is phenyl or substituted phenyl and the alkyl moiety has from 1 to 10 carbon atoms.

* * * * *